(12) United States Patent
Sauer et al.

(10) Patent No.: US 7,251,352 B2
(45) Date of Patent: Jul. 31, 2007

(54) MARKING 3D LOCATIONS FROM ULTRASOUND IMAGES

(75) Inventors: Frank Sauer, Princeton, NJ (US); Ali Khamene, Plainsboro, NJ (US); Benedicte Bascle, Plainsboro, NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 748 days.

(21) Appl. No.: 10/222,308

(22) Filed: Aug. 16, 2002

(65) Prior Publication Data

US 2003/0055335 A1 Mar. 20, 2003

Related U.S. Application Data

(60) Provisional application No. 60/312,872, filed on Aug. 16, 2001, provisional application No. 60/312,876, filed on Aug. 16, 2001, provisional application No. 60/312,871, filed on Aug. 16, 2001, provisional application No. 60/312,875, filed on Aug. 16, 2001, provisional application No. 60/312,873, filed on Aug. 16, 2001.

(51) Int. Cl.
*G06K 9/00* (2006.01)
*G09G 5/00* (2006.01)

(52) U.S. Cl. .................. 382/128; 382/103; 382/154; 345/156

(58) Field of Classification Search ............ 382/128, 382/103, 154; 345/156
See application file for complete search history.

(56) References Cited

U.S. PATENT DOCUMENTS

| | | | | |
|---|---|---|---|---|
| 3,805,028 A | * | 4/1974 | Morton | 382/133 |
| 5,148,809 A | * | 9/1992 | Biegeleisen-Knight et al. | 600/443 |
| 5,538,004 A | * | 7/1996 | Bamber | 600/443 |
| 5,694,142 A | * | 12/1997 | Dumoulin et al. | 345/9 |
| 5,787,889 A | * | 8/1998 | Edwards et al. | 600/443 |
| 5,810,007 A | * | 9/1998 | Holupka et al. | 600/439 |
| 5,928,151 A | * | 7/1999 | Hossack et al. | 600/443 |
| 6,019,724 A | * | 2/2000 | Gronningsaeter et al. | 600/439 |
| 6,047,080 A | * | 4/2000 | Chen et al. | 382/128 |
| 6,064,749 A | * | 5/2000 | Hirota et al. | 382/103 |
| 6,108,439 A | * | 8/2000 | Ishiguro | 382/131 |
| 6,190,320 B1 | * | 2/2001 | Lelong | 600/439 |
| 6,231,508 B1 | * | 5/2001 | Miller et al. | 600/437 |

(Continued)

OTHER PUBLICATIONS

State, A., Mark L., Gentaro H., William G., Mary W., Henry F., and Etta P. (MD). "Technologies for Augmented-Reality Systems: realizing Ultrasound-Guided Needle Biopsies." Proceedings of SIGGRAPH 96, pp. 439-446.*

X. Zhang and N. Navab. Tracking and pose estimation for computer assisted localization□□in industrial environments. In WACV, pp. 214-221, Palm Springs, CA, Dec. 2000.*

(Continued)

*Primary Examiner*—Matthew C. Bella
*Assistant Examiner*—Utpal Shah
(74) *Attorney, Agent, or Firm*—Michael L. Conover

(57) ABSTRACT

A method for marking three-dimensional (3D) locations from images obtained from an ultrasound imaging system including a transducer, comprising the steps of: tracking the pose of the transducer with respect to an external 3D coordinate system; obtaining a two-dimensional (2D) ultrasound image from the transducer; marking a desired target with a marker on the 2D ultrasound image; and calculating the 3D position of the marker utilizing data from the step of tracking.

20 Claims, 1 Drawing Sheet

U.S. PATENT DOCUMENTS

| | | | |
|---|---|---|---|
| 6,330,356 B1 * | 12/2001 | Sundareswaran et al. | 382/154 |
| 6,396,497 B1 * | 5/2002 | Reichlen | 345/427 |
| 6,445,815 B1 * | 9/2002 | Sato | 382/154 |
| 6,514,201 B1 * | 2/2003 | Greenberg | 600/437 |
| 6,675,040 B1 * | 1/2004 | Cosman | 600/427 |
| 6,678,546 B2 * | 1/2004 | Toker et al. | 600/436 |
| 6,724,930 B1 * | 4/2004 | Kosaka et al. | 382/154 |
| 6,765,569 B2 * | 7/2004 | Neumann et al. | 345/419 |
| 6,922,484 B2 * | 7/2005 | Asano et al. | 382/154 |
| 2003/0011624 A1 * | 1/2003 | Ellis | 345/646 |

OTHER PUBLICATIONS

U. Neumann and Y. Cho. A selftracking augmented reality system. In Proceedings of the ACM Symposium on Virtual Reality and Applications, pp. 109-115, Jul. 1996.*

Kato H. and Billinghurst M., "Marker Tracking and HMD Calibration for a Video-Based Augmented Reality Conferencing System", Proceedings of the 2nd IEEE and ACM International Workshop on Augmented Reality, pp. 85, 1999.*

* cited by examiner

MARKING 3D LOCATIONS FROM ULTRASOUND IMAGES

CROSS REFERENCE TO RELATED UNITED STATES APPLICATIONS

Reference is hereby made to the following U.S. Provisional patent applications whereof the benefit is hereby claimed and the disclosures hereby incorporated by reference:

U.S. Provisional patent application No. 60/312,872, entitled MARKING 3D LOCATIONS FROM ULTRASOUND IMAGES and filed Aug. 16, 2001 in the names of Frank Sauer, Ali Khamene, Benedicte Bascle;

U.S. Provisional patent application No. 60/312,876, entitled LOCAL 3D RECONSTRUCTION FROM ULTRASOUND IMAGES and filed Aug. 16, 2001 in the names of Frank Sauer, Ali Khamene, Benedicte Bascle;

U.S. Provisional patent application No. 60/312,871, entitled SPATIOTEMPORAL FREEZING OF ULTRASOUND IMAGES IN AUGMENTED REALITY VISUALIZATION and filed Aug. 16, 2001 in the names of Frank Sauer, Ali Khamene, Benedicte Bascle;

U.S. Provisional patent application No. 60/312,875, entitled USER INTERFACE FOR AUGMENTED AND VIRTUAL REALITY SYSTEMS and filed Aug. 16, 2001 in the names of Frank Sauer, Lars Schimmang, Ali Khamene; and U.S. Provisional patent application No. 60/312,873, entitled VIDEO-ASSISTANCE FOR ULTRASOUND GUIDED NEEDLE BIOPSY and filed Aug. 16, 2001 in the names of Frank Sauer and Ali Khamene.

Reference is hereby made to the following copending U.S. patent applications being filed on even date herewith.

U.S. patent application Ser. No. 10/222,182, entitled LOCAL 3D RECONSTRUCTION FROM ULTRASOUND IMAGES and filed in the names of Frank Sauer, Ali Khamene, Benedicte Bascle;

U.S. patent application Ser. No. 10/222,333, entitled SPATIOTEMPORAL FREEZING OF ULTRASOUND IMAGES IN AUGMENTED REALITY VISUALIZATION and filed in the names of Frank Sauer, Ali Khamene, Benedicte Bascle;

U.S. patent application Ser. No. 10/222,284, entitled USER INTERFACE FOR AUGMENTED AND VIRTUAL REALITY SYSTEMS and filed in the names of Frank Sauer, Lars Schimmang, Ali Khamene; and U.S. patent application Ser. No. 10/222,170, entitled VIDEO-ASSISTANCE FOR ULTRASOUND GUIDED NEEDLE BIOPSY and filed in the names of Frank Sauer and Ali Khamene.

FIELD OF THE INVENTION

The present invention relates to imaging and, more specifically to ultrasound imaging.

DESCRIPTION OF THE RELATED ART

Ultrasound scanners are commonly utilized to capture live 2D images from within objects or patients. Scanners typically have a standard option to freeze an image in time and display the still image on the screen for evaluation, e.g. for measuring spatial dimensions in the image.

Helpful background material on augmented reality and related topics can be found in Proceedings of the IEEE and ACM International Symposium on Augmented Reality 2000, dated Oct. 5-6, 2000; Munich, Germany; IEEE Computer Society, Los Alamitos, Calif., U.S.A. In the above-cited Proceedings, an article of particular interest entitled AUGMENTED WORKSPACE: DESIGNING AN AR TESTBED is published on pages 47-53, and is authored by Frank Sauer, an inventor in the present application, et alii.

See also the review article by R. T. Azuma: "A Survey of Augmented Reality", Presence: Teleoperators and Virtula Environments, 6(4), 355-386, (1997).

SUMMARY OF THE INVENTION

FIG. 1 shows a schematic block diagram of such an augmented reality system as may be utilized in conjunction with features of the invention. A tracker camera 10 is coupled by way of an A/D (analog to digital) converter 12 to a programmable digital computer 14. Two scene cameras 15 are coupled to computer 14. An ultrasound scanner 16, having a transducer 18, is coupled by way of an A/D converter 20 to computer 14. A head-mounted display (HMD) control unit 22 is coupled for signal interchange with computer 14 and to an HMD display 24.

In accordance with an aspect of the present invention, a method is provided for marking (or outlining) of targets on an ultrasound slice in the 2-dimensional (2D) ultrasound slice plane and in 3 dimensions (3D).

In accordance with another aspect of the present invention, a system tracks the pose of the transducer used in the ultrasound scanner, and hence the pose of the ultrasound slice, with respect to a fixed external 3D coordinate system.

In accordance with another aspect of the present invention, a system provides an interface to the user that enables the user either to directly mark a desired target in an ultrasound image, or trigger the system to (semi)automatically locate a target in a given ultrasound image.

In accordance with another aspect of the invention, a method for marking three-dimensional (3D) locations from images obtained from an ultrasound imaging system including a transducer, comprising the steps of: tracking the pose of the transducer with respect to an external 3D coordinate system; obtaining a two-dimensional (2D) ultrasound image from the transducer; marking a desired target with a marker on the 2D ultrasound image; and calculating the 3D position of the marker utilizing data from the step of tracking.

BRIEF DESCRIPTION OF THE DRAWINGS

The invention will be more fully understood from the following detailed description of preferred embodiments, in conjunction with the Drawing in which the FIG. 1 shows a system block diagram of an augmented reality system.

DETAILED DESCRIPTION OF THE PREFERRED EMBODIMENTS

Figure 1:
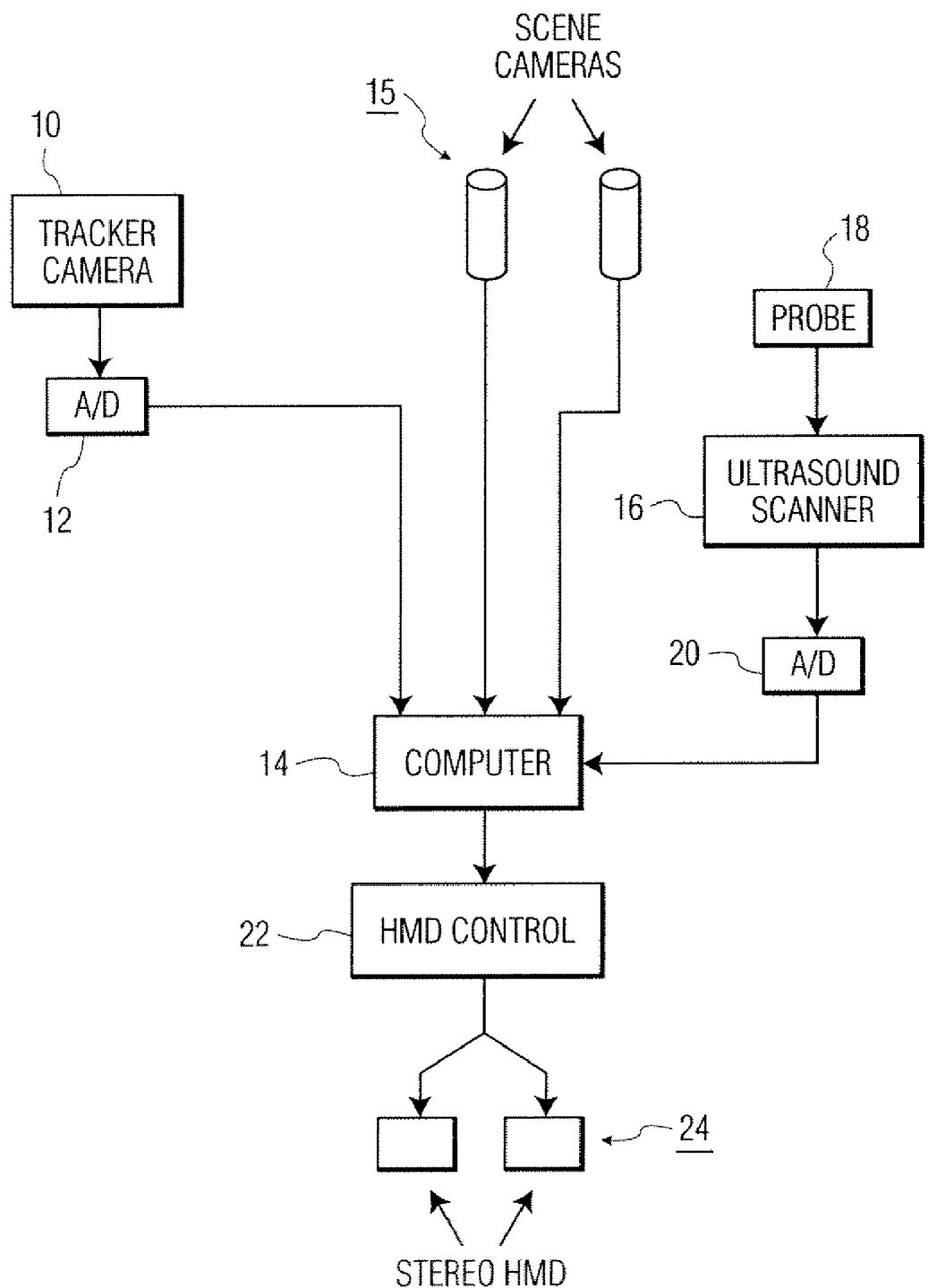

In accordance with a preferred embodiment, an ultrasound scanner, including a transducer, is utilized for imaging. The user is provided with augmented reality visualization, where the ultrasound slices are overlaid onto a view of the patient/object in a registered manner. Tracking apparatus is provided for tracking the transducer and for tracking the user's viewpoint for the augmented reality application. Such augmented reality application techniques, whereby structures that are visible in the ultrasound images appear in the location of the corresponding physical structures are, per se, known in the art and need not be set forth in detail.

Preferably, the augmented view is stereoscopic to provide the user with depth perception. A calibration procedure is provided and the equipment is coupled to a computer for generating the graphics required and providing the necessary image processing.

Furthermore, a local user interface is provided in accordance with the principles of the present invention.

With the user interface, a user can initiate the target localization and marking.

In accordance with the present embodiment, the user interface is equipped with a pointing device, such as a computer-type mouse, coupled to the computer.

In operation, a user can use the pointing device, such as a mouse, to mark a 2D location in the image. With the knowledge of the 3D pose of that image, the system calculates the 3D position of the marker. The user's input may be in an "on-line" mode, where he holds the transducer still in the desired pose, or in an "off-line" mode, where the user first freezes, that is, records the image, together with its pose information, and then places the marker in the recorded still image at his leisure. For the on-line mode, the pointing device is preferably attached to the transducer and can be operated with the same hand that is holding the transducer, or alternatively, it is placed on the floor and operated by way of a foot-pedal.

In accordance with another preferred embodiment, the system performs image processing on an ultrasound image and automatically, or semi-automatically, locates a target of a type optionally predetermined by the user. The input required of the user is thereby simplified. For example, without an extra pointing device, the user may place the transducer in a pose where the target structure appears on the vertical centerline of the ultrasound image. The user then triggers the system to locate the target along the image's centerline such as by using a button on the transducer, by operating a foot-switch, by using voice control, or any other convenient control device. The system in accordance with the present embodiment includes a processor that searches the image along its centerline, which makes locating the target easier than if the search would have to be conducted over the whole image.

A preferred search algorithm would be to de-noise the image around the centerline, for example, with a median filter, identify potential target locations in a line scan along the centerline, and verify the existence of a target with, for example, a Hough transform. The Hough transform is known and may be found in various textbooks, such as, for example, "Fundamentals of Electronic Image Processing" by Arthur R. Weeks, Jr., IEEE Press, New York, N.Y.; 1996.

When the system proposes a target location, the user then accepts or rejects the proposed location with another trigger input by using a button on the transducer, a footswitch, voice control, etc.

As an alternative to using a line on the ultrasound image as pointer, a line other than the vertical centerline can be used, such as a vertical off-center line, or a line that is tilted at an angle with respect to the vertical direction.

A target position along a line can be input by user via a thumbwheel at transducer or a similar one-dimensional (1D) pointing device for which no image processing is necessary.

In an alternative embodiment, the user uses a line on the ultrasound image to point to target from two different transducer poses, so that the system can calculate the target location as the intersection of the two lines in 3D space. Alternatively two different lines can be used to require less movement between the two pointing transducer poses, for example, two lines that intersect in the image.

The image processing is powerful enough to find a target in the 2D image. The user need then only position the transducer so that the target is visible in the image, initiate the automatic target search, and then confirm or reject a target proposed by the system. Several targets can be found in the same image. This embodiment is attractive from a user point of view as it requires the least input; however, robust target detection in ultrasound images is difficult. Therefore, there are advantages to providing the user with a 1D or 2D pointing interface as described in the above embodiments.

The system thus graphically marks confirmed target locations and records the respective 3D coordinates thereof. Preferred visualization is in a stereoscopic augmented or virtual reality fashion.

Instead of just marking the target location as the target center, the system can also perform image processing to obtain an outline of the target, and show this outline in a graphical representation.

Marking of the 3D locations of target structures can be helpful for diagnostic purposes, for guidance of interventional procedures, as well as for registering the ultrasound images to images taken with other imaging modalities like CT (computer tomography) and MR. (magnetic resonance imaging).

While the invention has been explained by way of exemplary embodiments, it will be understood by one of skill in the art to which it pertains that various modifications and changes may be readily made without departing from the spirit of the invention which is defined by the claims following. For example, where the claims refer to marking a target, this is to be understood to encompass deriving an outline of a target by image processing to present the outline by graphical representation.

What is claimed is:

1. A method for marking three-dimensional (3D) locations from images obtained from an ultrasound imaging system including a transducer, comprising the steps of:

tracking the pose of said transducer with respect to an external 3D coordinate system;

viewing a live two-dimensional (2D) ultrasound image produced by said transducer;

adjusting said pose of said transducer wherein a target appears in a designated part of said 2D ultrasound image for indicating marker location;

searching said designated part of said 2D ultrasound image to automatically locate a potential target of a predetermined type;

marking a location of said target with a marker; and calculating the 3D position of said marker utilizing data from said tracking step.

2. The method for marking of claim 1, wherein searching said designated part comprises de-noising said image around said designated part, identifying potential target locations along said designated part, and verifying the existence of said target.

3. The method for marking of claim 2, wherein verifying the existence of said target comprises performing a Hough transform.

4. The method for marking of claim 2, further comprising presenting a potential target location to a user, and accepting input from said user wherein said user accepts or rejects said potential target location.

5. The method for marking of claim 1, wherein said designated part is a vertical centerline of said 2D ultrasound image.

6. The method for marking of claim 1, wherein said designated part is a vertical off-center line in said 2D ultrasound image.

7. The method for marking of claim 1, wherein said designated part is a line tilted at an angle with respect to a vertical direction in said 2D ultrasound image.

8. The method for marking of claim 1, further comprising pointing to said target from different transducer poses, and calculating said target location as an intersection of lines through said poses.

9. The method for marking of claim 1, further comprising obtaining an outline of said target, and displaying a graphical representation of said outline.

10. The method for marking of claim 1, including a step of inputting a target position along said designated part by a pointing device.

11. A program storage device readable by a computer, tangibly embodying a program of instructions executable by the computer to perform the method steps for A method for marking three-dimensional (3D) locations from images obtained from an ultrasound imaging system including a transducer, comprising the steps of:
- tracking the pose of said transducer with respect to an external 3D coordinate system;
- viewing a live two-dimensional (2D) ultrasound image produced by said transducer;
- adjusting said pose of said transducer wherein a target appears in a designated part of said 2D ultrasound image for indicating marker location;
- searching said designated part of said 2D ultrasound image to automatically locate a potential target of a predetermined type;
- marking a location of said target with a marker; and
- calculating the 3D position of said marker utilizing data from said tracking step.

12. The computer readable program storage device of claim 11, wherein searching said designated part comprises de-noising said image around said designated part, identifying potential target locations along said designated part, and verifying the existence of said target.

13. The computer readable program storage device of claim 12, wherein verifying the existence of said target comprises performing a Hough transform.

14. The computer readable program storage device of claim 12, the method further comprising presenting a potential target location to a user, and accepting input from said user wherein said user accepts or rejects said potential target location.

15. The computer readable program storage device of claim 11, wherein said designated part is a vertical centerline of said 2D ultrasound image.

16. The computer readable program storage device of claim 11, wherein said designated part is a vertical off center line in said 2D ultrasound image.

17. The computer readable program storage device of claim 11, wherein said designated part is a line tilted at an angle with respect to a vertical direction in said 2D ultrasound image.

18. The computer readable program storage device of claim 11, the method further comprising pointing to said target from different transducer poses, and calculating said target location as an intersection of lines through said poses.

19. The computer readable program storage device of claim 11, the method further comprising obtaining an outline of said target, and displaying a graphical representation of said outline.

20. The computer readable program storage device of claim 11, the method including a step of inputting a target position along said designated part by a pointing device.

* * * * *